United States Patent
Santucci et al.

(10) Patent No.: US 9,895,387 B2
(45) Date of Patent: Feb. 20, 2018

(54) **COMPOSITIONS FOR TREATING *HELICOBACTER PYLORI* INFECTION**

(75) Inventors: Annalisa Santucci, Siena (IT); Natale Figura, Siena (IT); Adriano Spreafico, Siena (IT); Giovanni Cavallo, Rome (IT); Roberto Filippo Marcolongo, Siena (IT); Paola Marcolongo, legal representative, Siena (IT)

(73) Assignee: OVER S.R.L., Siena (IT)

(*) Notice: Subject to any disclaimer, the term of this patent is extended or adjusted under 35 U.S.C. 154(b) by 0 days.

(21) Appl. No.: 13/700,084

(22) PCT Filed: May 26, 2011

(86) PCT No.: PCT/IT2011/000175
§ 371 (c)(1),
(2), (4) Date: Apr. 29, 2013

(87) PCT Pub. No.: WO2011/148405
PCT Pub. Date: Dec. 1, 2011

(65) Prior Publication Data
US 2013/0217641 A1    Aug. 22, 2013

(30) Foreign Application Priority Data
May 26, 2010 (IT) .............. RM2010A0274

(51) Int. Cl.
| A61K 31/4164 | (2006.01) |
| A61K 31/7048 | (2006.01) |
| A61K 31/765 | (2006.01) |
| A61K 45/06 | (2006.01) |
| A61K 31/4168 | (2006.01) |
| A61K 31/7034 | (2006.01) |
| A61K 31/77 | (2006.01) |

(52) U.S. Cl.
CPC ...... *A61K 31/7048* (2013.01); *A61K 31/4164* (2013.01); *A61K 31/4168* (2013.01); *A61K 31/7034* (2013.01); *A61K 31/765* (2013.01); *A61K 31/77* (2013.01); *A61K 45/06* (2013.01)

(58) Field of Classification Search
CPC ............ A61K 31/7048; A61K 31/4164; A61K 31/765; A61K 45/06
See application file for complete search history.

(56) References Cited

FOREIGN PATENT DOCUMENTS

| CN | 1179970 A | 4/1998 |
| CN | 1732969 A | 2/2006 |
| CN | 1947720 A | 4/2007 |
| EP | 1 803 450 A1 | 7/2007 |
| WO | WO 96/05822 A1 | 2/1996 |
| WO | WO 96/24375 A1 | 8/1996 |
| WO | WO 97/36600 A1 | 10/1997 |
| WO | WO 2011/080148 A2 | 7/2011 |

OTHER PUBLICATIONS

Siddaraju et al, J. Agric. Food Chem. 2007, vol. 56, pp. 7377-7386.*
Machine translation of CN 1947720 (2005).*
Kane, Anne V. et al.: "Unique susceptibility of Helicobacter pylori to simethicone emulsifiers in alimentary therapeutic agents," Antimicrobial Agents and Chemotherapy, 40 (2), 500-2 CODEN: AMACCQ; ISSN: 0066-4804, 1996, XP002605432.
Chinese Office Action issued in Chinese Patent Application No. 201180025432.2 dated Dec. 26, 2013.
Italian Search Report issued in Italian Patent Application No. RM20100274 dated Oct. 18, 2010.

* cited by examiner

*Primary Examiner* — Leigh C Maier
(74) *Attorney, Agent, or Firm* — Arent Fox LLP

(57) ABSTRACT

Pharmaceutical compositions for treating infection from *Helicobacter pylori*. are described, containing, as the active ingredients, polysorbate and an antibiotic selected from clarithromycin, metronidazole and a mixture thereof.
The invention also concerns the use of such compositions as anti-infective agents for the *H. pylori* eradication treatment, in particular in a combined therapy with a second antibiotic agent and with a gastric proton pump inhibiting agent, or an antacid, or an $H_2$ receptor antagonist, in a therapeutic protocol known as "triple therapy" for the treatment of peptic ulcer.

14 Claims, No Drawings

COMPOSITIONS FOR TREATING *HELICOBACTER PYLORI* INFECTION

CROSS-REFERENCED TO RELATED APPLICATION

This application is a National Phase entry of International Application PCT/IT2011/000175, filed May 26, 2011, which claims priority to Italian Patent Application No. RM2010A000274, filed May 26, 2010, the disclosure of the prior application(s) are hereby incorporated in their entirety by reference.

FIELD OF THE INVENTION

The present invention concerns compositions for treating infection from *Helicobacter pylori*. More specifically, the invention concerns the use as anti-infective agents of antibiotic compositions containing, as the active ingredients, combinations of a known emulsifying and non-ionic surface active agent, i.e. polysorbate, with one of two specific antibiotics already in use for the *H. pylori* eradication treatment.

BACKGROUND OF THE INVENTION

As it is known, *Helicobacter pylori* is a helix-shaped Gram-negative microaerophilic microorganism that can inhabit the stomach and the duodenum, adapting itself to the inhospitable environment of the gastric mucosa in a quite particular way, to the point that it often fails to produce any detectable symptoms. Actually, it is considered that more than 80% of the individuals infected with *H. pylori* are asymptomatic. Such microorganism infects more than half of the world population at the level of the gastro-duodenal tract. The transmission route of the infection has not been clarified, although infection seems to be typically acquired in the childhood.

The stomach is protected from its own gastric juice, made of concentrated hydrochloric acid and rich of digestive enzymes, by a thick layer of mucus which covers the gastric mucosa and within which the *Helicobacter* may penetrate and survive, resisting to the possible acid that may reach it thanks to an enzyme produced by such bacterium, urease. Urease converts the urea contained in large amounts in the stomach into bicarbonate and ammonium. Therefore, a basic environment Is established in the vicinity of the bacterial colony, such environment being capable of neutralizing the hydrochloric acid of gastric secretions, thereby protecting *H. pylori*.

Another protective mechanism available to *Helicobacter pylori* consists in that the natural immune defenses of the body cannot reach it in the gastric mucus. The immune system reacts to the *H. pylori* infection by sending leukocytes, killer T lymphocytes and other defense factors, but these cannot reach the infection site, as they cannot easily penetrate through the mucus layer, and remain and accumulate in the site, leaving there their destructive content (consisting of superoxide radicals) when they die. Additional nutrients are sent on the site to assist the white blood cells, and this fact does no more than further feeding *Helicobacter* itself. As a result, a gastritis develops in a few days, which may sometimes progress up to peptic ulcer. In view of the foregoing, it is considered that the causative agent of the damage to the gastric mucosa is not *H. pylori* itself, but the inflammation and, consequently, the immune response to the microorganism.

From the scientific literature it appears that infection from *Helicobacter pylori* is the main cause of chronic gastritis and the most relevant factor for the development of peptic ulcer (Warren J R, Marshall B J. *Unidentified curved bacilli on gastric epithelium in active chronic gastritis*. Lancet 1983; 1:1273-5). By colonizing the stomach, *H. pylori* induces a persistent inflammation (chronic gastritis) which may last years without developing with clinical symptoms. However, in 10-20% of the cases, it may result in the development of gastric or duodenal ulcers.

Also gastric cancer (gastric adenocarcinoma and non-Hodgkin gastric lymphoma) is often associated with *H. pylori* (Moss S F. *The carcinogenic effect of H. pylori on the gastric epithelial cell*. J Physiol Pharmacol 1999; 50:847-56). In the frame of a wide review of cases of gastric carcinoma it has been shown that the presence of *H. pylori* results in a six-fold increase of the risk of gastric cancer. I is believed that chronic gastritis may lead to intestinal metaplasia, which in turn, may degenerate into malignant cancer. The low grade malignant lymphoma o MALToma, in turn, seems to derive from the malignant degeneration of lymphoid tissue associated with the mucosa. In this case, retrospective bioptic studies demonstrated that 90% of these MALTomes are associated he presence of *H. pylori*.

The various strains of *Helicobacter pylori* are not endowed with the same pathogenic power: strains having in their chromosome an insertion defined "cag pathogenicity island" (cagPAI), a set of genes involved in the virulence of the microorganism, exhibit a higher inflammatory potential. About 50-70% of the *H. pylori* strains found in western countries contain the cag pathogenicity island, and the patients infected with bacteria containing the cag PAI have a stronger gastric inflammatory response and a higher risk of developing peptic ulcers or gastric cancer compared to patients infected with strains that do not contain such insertion in their genome. The cag-positive strains are able to inject in the colonized gastric cells an oncoprotein (codified by one the cag genes) named cagA, which increases the risk of developing neoplastic lesions (Censini S, Lange C, Xiang Z, Crabtree J E, Ghiara P, Borodovsky M, et al. *cag, a pathogenicity island of Helicobacter pylori, encodes type I-specific and disease-associated virulence factors*. Proc Natl Acad Sci USA 1996; 93:14648-53).

Once the infection from *Helicobacter pylori* has been diagnosed in patients with peptic ulcer, the normal procedure consists in eradicating pharmacologically the microorganism, thus allowing the ulcer to heal. At present, the first choice standard treatment, known as "triple therapy" consists in the administration of:
  a) a gastric proton pump inhibitor;
  b) two antibiotics, selected from amoxicillin, clarithromycin, metronidazole or tetracycline.

As it is known, the gastric proton pump is a metabolic mechanism typical of the stomach lining cells which allows them to secrete hydrochloric acid in the gastric juice. The gastric pump inhibitors are a group of molecules the main action of which is to reduce for a long term (from 18 to 24 hours) the acidity of gastric juice. They act through the inhibition of the gastric enzyme H+/K+-ATPase (the proton pump), i.e. the catalyst of the H+ and K+ ions exchange.

Such active ingredients, the most widespread of which are omeprazole, lansoprazole and esomeprazole, lead to a remarkable reduction of the gastric acidity, and are therefore used in the treatment of dyspepsia, gastro-oesophageal reflux and peptic ulcer, where they have practically replaced the drugs previously in use for similar indications, i.e. histamine $H_2$ receptor antagonists or $H_2$ anti-histamines, as ranitidine and cimetidine.

In the *H. pylori* eradication treatment, the proton pump inhibitors are used to alleviate the symptoms of peptic ulcer and to facilitate the actions of antibiotics, while the proper eradication action is carried out by the latter, which are administered with the precautions and limitations typical of any antibiotic treatment.

In the course of the years, the therapeutic protocols have progressively improved, allowing to go, in standard cases, from therapies of two weeks to therapies of 7 or 10 days, thus reducing the number of dosage units to be administered daily and limiting the toxicity and side effects of the same. Alternative protocols have been developed in case of allergies to specific drugs; second line treatment schedules have been designed in case of failure of the first cycle of therapy, and the overall eradication efficacy has improved, affording success rates of at least 80%. The case of undesired effects are kept within a limit of 10-15% of the patients, and normally such effects are not so serious to result in abandonment of the therapy.

Such undesired effects, both local and systemic, however, make the said therapy poorly tolerable. The most common of such side effects are, apart from cases of true intolerance to the active ingredient, dizziness and sense of confusion, oral bad taste, nausea and digestive or intestinal discomfort.

In addition, and more critically, an ever increasing number of patients appears to be infected by resistant bacteria: in most of the world several clarithromycin-resistant strains have been already evidenced, as well as metrodinazole-resistant strains. For the patients infected by resistant *H. pylori* strains the use of alternative antibiotics has been proposed, to be possibly exploited in case of failure of the first treatment cycle. For instance, for the treatment of clarithromycin-resistant strains the use of levofloxacin has been suggested, in a second-line triple therapy (Perna F, Zullo A, Ricci C, Hassan C, Morini S, Vaira D. *Levofloxacin-based triple therapy for Helicobacter pylori re-treatment: role of bacterial resistance. Dig Liver Dis,* 2007, 39(11):1001-5).

In the light of the foregoing, it is evident that pharmacological therapies for the eradication of *Helicobacter pylori* require continuous revision and updating, not only in order to improve the efficacy or tolerability of the drugs, but also as a consequence of the evolution of antibiotics-resistant strains in some populations, also depending on the use the various antibiotics in the different territories.

As recent studies have shown that the addition of substances having scavenging activity against free radicals, such as vitamin C, to the medicaments used to treat *H. pylori* infections improves the eradication rates, the interest of microbiologists and clinicians has concentrated on biologically active natural compounds, in particular plant extracts, known for being provided with antioxidant and/or antibacterial activity. The latter should be combined with the pharmacological therapies or should be used as nutritional supplements (Correa P, Malcom G, Schmidt B, Fontham E, Ruiz B, Bravo J C, et al. *Antioxidant micronutrients and gastric cancer. Aliment Pharmacol Ther* 1998; 1: 73-8). Several studies has shown the antibacterial effect of a wide variety of fruits and derivatives thereof, such as berries, garlic, onion, kiwi, citrus fruits and wine, as well as extracts from plant and drugs, in particular essential oils, cinnamon, thyme, propolis, licorice, paprika, tea and rice (see, for istance, Nostro A, Cellini L, Di Bartolomeo S, Di Campli E, Grande R, Cannatelli M A, et al. *Antibacterial effect of plant extracts against Helicobacter pylori. Phytother Res* 2005; 19:198-202; e Ohno T, Kita M, Yamaoka Y, Imamura S, Yamamoto T, Mitsufuji S, et al. *Antimicrobial activity of essential oils against Helicobacter pylori. Helicobacter* 2003; 8:207-15).

In such a frame, some of the present authors have recently studied and identified the phenolic compounds present in the thorn bush leaves (*Rubus ulmifolius*) and in the common wheat flour, and have ascertained the antioxidant activity and antibacterial power thereof against *H. pylori* strains (Martini S, D'Addario C, Colacevich A, Focardi S, Borghini F, Santucci A, Figura N, Rossi C. *Antimicrobial activity against Helicobacter pylori strains and antioxidant properties of blackberry leale (Rubus ulmifolius) and isolated components. Int. J Antimicrob Agents.* 2009; 34:50-9).

Amongst the phenolic components most abundantly present in such extracts there is ferulic acid, a lignin component making up the vegetal cell walls, that is largely found in rice, wheat and other cereals, as well as in coffee and in different seeds and fruits. The antioxidant properties of ferulic acid have led to propose its use in a wide variety of therapeutic applications for the prevention and treatment of pathologies ranging from cancer to neurodegenerative diseases, to diabetes, cardiovascular dysfunctions and also in the field of peptic ulcer and for the treatment of *H. pylori* infections, through several vegetal extracts containing it.

Considering the various further substances that have been proposed as active ingredients or adjuvants in the pharmacological treatment of *Helicobacter pylori* eradication in view of their antibacterial properties, the international patent application publ. No. WO 96/05822 (New England Medical Center Hospital) discloses the use of some molecules normally employed as non-ionic surfactants and emulsifiers, suitable for use in foods, cosmetics and pharmaceutical products, among which, specifically, polysorbates. Such compounds are a class of substances derived from polyethoxylated or PEG-ylated sorbitan ((3S)-2-(1,2-dihydroxyethyl)tetrahydrofuran-3,4-diol, a cyclic polyhydroxy compound obtained from the dehydration of sorbitol), having the four hydroxyl groups etherified with polyethylene glycol chains, in turn esterified with a fatty acid chain (monolaurate, monopamitate, monostearate or monooleate).

The polysorbates known with the commercial name Tween are often used in view of their solubilising properties as emulsifiers and antifoam additives in fermentations. Starting from experimentations on *Helicobacter pylori* cultures, the authors of the cited patent application have found that such compounds behave as potent inhibitors of bacterial growth. For such reasons the cited document proposes the administration of polysorbate-based compositions for the treatment of *H. pylori* infections in the frame of a sequential eradication treatment, wherein, however, any temporal overlapping between the antibiotic treatment and the treatment with polysorbate it is absolutely excluded.

As a matter of fact it had been found that the proposed surface active/emulsifying agents have bactericidal activity at some given concentrations, but only bacteriostatic activity at lower concentrations, and inhibit the *H. pylori* growth without totally eradicating it. Since many antibiotics used in clinics are active only on microorganisms being in an active growth phase, the simultaneous presence of the surface active/emulsifying agent proposed and the antibiotic would have been counterproductive. The therapy proposed by the cited document consists, therefore, in administering the known antibiotics for the treatment of *Helicobacter* in the absence of the proposed surfactant/emulsifying agent and, thereafter, administering such agent alone.

Also the international patent application publ. No, WO 97/36600 (AMBI Inc.), filed sometime later, proposes the use of polysorbates-containing compositions in the treatment of gastrointestinal disorders caused by *H. pylori*. The authors report to have found that polysorbates, in particular, non only inhibit *H. pylori* growth, but rapidly kill said bacterial strains, and therefore they may be used alone in the eradication of the microorganism. The cited document describes the use of polyoxyethilene sorbitan (and in particular polysorbate 20, which is the monolaurate ester of polysorbate) alone or in combination with other known antiulcer agents, including $H_2$ receptor antagonists, bismuth salts, antacids and proton pump inhibitors and, specifically, in combination with mucolytic agents, but not in combination with systemic antibiotics. On the contrary, the administration together with antibiotics, which may be absorbed in the systemic circulation or pass through the intestine, is expressly not recommended.

SUMMARY OF THE INVENTION

On the grounds of such prior art, an object of the present invention is, thus, to provide new pharmaceutical preparations for the treatment of *Helicobacter pylori* infections having improved activity and tolerability, and able to treat more successfully the resistant bacterial strains, while not excessively departing from the therapeutic protocols already consolidated for the pharmacological treatment of *H. pylori* eradication.

Based on the studies carried out in the frame of the present invention, it has been found that, differently from what suggested by the prior art, the combinations of the non-ionic surface active/emulsifying agents known by the common name polysorbates and by the commercial name Tween and with two of the antibiotics currently used for the eradication treatment of *H. pylori*, specifically metrodinazole and clarithromycin, show an unexpected synergistic activity, and result in compositions surprisingly effective also against strains resistant to the said antibiotics.

DETAILED DESCRIPTION OF THE INVENTION

Therefore, the present invention specifically provides pharmaceutical compositions for the treatment of infection from *Helicobacter pylori* containing, as active ingredients, polysorbate and an antibiotic selected from clarithromycin, metronidazole and a mixture of the same, characterized in that the weight ratio of polysorbate to antibiotic or mixture of antibiotics is from 0.5:5 to 5:1.

For the purposes of the present description polysorbates are in general intended to be the esters polyoxyethylene (20) sorbitan and lauric, palmitic, stearic or oleic acid, wherein the digit 20 represents the total number of oxyethylene units of the molecule. In particular, polysorbate 80 or Tween 80 is polyoxyethylene (20) sorbitan monooleate, polysorbate 20 or Tween 20 is polyoxyethylene (20) sorbitan monolaurate, polysorbate 40 or Tween 40 is polyoxyethylene (20) sorbitan monopalmitate and polysorbate 60 or Tween 60 is polyoxyethylene (20) sorbitan monostearate.

According to a preferred embodiment of the invention, the antibiotic that is formulated in combination with polysorbate is clarithromycin, while according to another equally preferred embodiment said antibiotic is metronidazole. Indeed, it has found through the experimentation connected to the present research, for instance, that the activity of polysorbate when used in combination with the specific antibiotics metronidazole and clarithromycin is of the synergistic type, as the minimal bactericide concentrations (CMB, or MBC) of either of polysorbate and antibiotic when used in combination are several times lower (8 times lower for clarithromycin in a polysorbate-clarithromycin combination) than the CMB of the two substances separately tested.

Preferably, according to the invention, the polysorbate employed is polysorbate 80. Such product is already widespread as emulsifier in food products, in particular in the production of ice cream, in pharmaceutical products for parenteral administration, as antifoaming additive, in bacterial cultures, for instance for the production of vaccines, and is considered to be a safe and well tolerated product in humans.

Based on the results of a repeated toxicity study of 13 weeks in rats treated with polysorbate 60, it has been established that the minimum NOAEL (NO Adverse Effect Level) for the class of polysorbates is 1000 mg/kg (day. The latter, therefore, represents the maximum preclinical dose free from side effects. Once established the NOAEL=100 mg/kg/day, in order to fix the ADI (Accettable Daily Dose) for humans, a safety factor equal to 100 is applied, and consequently the present ADI is fixed to 10 mg/kg/day. Therefore, the dose considered to be free from side effects both from a food point of view and from the regulatory point of view for polysorbate is about 700-750 mg/day for an adult and 200 mg/day for a child. Such limit is largely prudential, however it can be exceeded, even slightly, for strictly pharmaceutical purposes.

The polysorbates are oily liquids at room temperature; in particular, polysorbate 80 appears to be a viscous water-soluble yellow liquid. A pharmaceutical composition according to the invention, based on polysorbate and an antibiotic selected from metronidazole and clarithromycin or mixtures thereof, may be preferably formulated in a pharmaceutical preparation in the form of a solution, colloidal suspension, emulsion, syrup or granulate. The administration in fluid form appears to be advantageous in view of its immediate ability to disperse onto the stomach walls.

According to some preferred embodiments of the invention, the proposed preparation is formulated in such a way that each dosage unit of the said composition—liquid, semisolid or solid—contains from 500 to 750 mg of polysorbate and 500 mg clarithromycin or 500 mg metronidazole.

Accordingly, considering that in the standard triple therapy for the eradication of *Helicobacter* the dosage of antibiotic is 500 mg twice a day (excluding amoxicillin, the usual dosage of which is 1 g twice a day), it is possible to propose a formulation, for instance in the form of a syrup, containing, in each dosage unit equal to 10 or 20 ml, a predetermined amount of 500-750 mg of polysorbate 80 and an amount of 500 mg of antibiotic (clarithromycin or metronidazole). Such preparation should be administered twice daily, in a dosage of 10 or 20 ml by volume (1 or 2 tablespoons).

In a therapy similar to the standard triple therapy, therefore, a treatment performed with the polysorbate-antibiotic combination of the invention can be effected, for instance, according to the following schedule:

omeprazole 20 mg twice daily;
amoxicillin 1 g twice daily;
polysorbate 80-clarithromycin syrup (or polysorbate 80-metronidazole syrup) 10 ml twice daily (equivalent, e.g., to 500 mg of polysorbate+500 mg of antibiotic twice daily).

According to some further preferred embodiments of the invention, the pharmaceutical composition proposed also contains, as a further active ingredient, ferulic acid. The purpose of adding ferulic acid to polysorbate is to exploit its antioxidant and antibacterial action against *H. pylori*, already described in the foregoing. Actually, as noted above, recent studies have demonstrated that the addition of substances having scavenging activity against free radicals, such as vitamin C, to the agents used to treat *H. pylori* infections increases the eradication rates.

As shown in the formulation examples reported below, pharmaceutical preparations particularly preferred in view of their practicality of realization and use in the eradication treatment of *H. pylori* are sachets of powder or granulated product, normally containing 4 g of preparation, to be dispersed in a glass of water before administration, or the syrup forms with dosing cap, wherein the antibiotic (or the antibiotics mixture) is contained with part of the excipients in the dosing cap, while the polysorbate, with another part of the excipients and the water required, are contained in form of a solution in the bottle. Similar embodiments allow a wide versatility in the definition of the formulation.

Specifically, the respective ratios of the various active agents can be selected from a wide range of proportions. According to some preferred embodiments of the invention, some of which are described further below, the ratio by weight of polysorbate 80 to antibiotic or antibiotics mixture is comprised between 1:5 and 4:1 (polysorbate/antibiotic).

It is also possible to foresee a further use of the active compounds proposed according to the invention in support of the antibiotic treatment for *H. pylori* eradication. Thus, ferulic acid and polysorbate can be included in a preparation, for instance a syrup, not containing the antibiotic, and containing, for instance, besides polysorbate and ferulic acid, vitamin E or derivatives thereof, e/or probiotics for the protection of intestinal bacterial flora.

A possible preparation that may be used for this purpose is a syrup containing, for instance, 5% polysorbate 80, 1% ferulic acid, 0.5% PEG-ylated vitamin E (and, optionally, some probiotics), to be administered in doses of 10 ml 2 times/day, as a support of the *H. pylori* eradication treatment.

According a further aspect thereof, the present invention provides the use for the treatment of infection from *Helicobacter pylori* of a combination of polysorbate and antibiotic selected from clarithromycin, metronidazole and a mixture thereof, wherein the weight ratio of polysorbate and antibiotics or mixture of antibiotics is comprised between 0.5:5 and 5:1.

As already noted, in some preferred embodiments of the invention the proposed preparation is a combination of polysorbate and clarithromycin, while in other such forms the preparation is a combination of polysorbate and metronidazole. In all cases, the type of polysorbate which is preferably included in the formulation is polysorbate 80, and formulation also comprises, preferably, ferulic acid as an antioxidant and coadjuvant of the antibacterial activity of the formulation.

It is to be noted that combinations and preparations of the same kind as those proposed according to the invention for the treatment of infection from *Helicobacter pylori* in humans can also be foreseen for veterinary use, for the treatment of similar bacterial species colonizing the oral cavity e the gastro-intestinal apparatus of animals.

*H. pylori* species which can be interested by veterinary treatments include, for instance *H. canis* and *H. felis*, representing the corresponding pathogens for dogs and cats.

As it is evident the pharmaceutical composition proposed according to the invention may be employed in general as antibacterial in the treatment of infections from bacteria sensitive to metronidazole or clarithromycin, but it is specifically proposed for use in the frame of an eradication treatment for *Helicobacter pylori*. Such treatment comprises the simultaneous administration of another antibiotic belonging to the group of antibiotics already consolidated for the treatment in question, first of all amoxicillin.

More preferably, as it will be evident in the further below, the treatment with the preparation according to the invention may be applied in cases where the *Helicobacter* to be eradicated belongs to a strain resistant to clarithromycin and/or to metronidazole.

EXAMPLES

The present invention is being also described, for merely illustrative purposes, in the following examples, showing possible formulations based on polysorbate, clarithromycin and/or metronidazole for use in the treatment of infection from *H. pylori* as proposed according to the invention. The formulations for two different pharmaceutical forms are reported in the following examples:

product in powder, 4 grams sachet, to be dispersed in a glass of water before administration;

product in solution, syrup to be prepared before use, consisting of a dosing cap containing the antibiotics and a 20 ml bottle containing the polysorbate 80 solution.

Formulations Containing Clarithromycin, Metronidazole and Polysorbate 80

A. 4 Grams Sachets of Powder Product

For each one of the following examples a first mixture (Antibiotic mixture) is prepared, containing the antibiotics and part of the excipients. A second mixture is prepared (Surfactant mixture) containing polysorbate 80 and another part of the excipients. The two mixtures are then joined and mixed in the proportions shown in the table for each one of the following examples.

The division in two parts evidences that polysorbate 80 does not have a technological function, rather it is a true active ingredient which is prepared separately from the antibiotic mixture.

Example 1—Preparation with Polysorbate/Antibiotics Ratio: 1:5

| Ingredients | Weight (g) | Active ingredients (g) |
|---|---|---|
| Antibiotic mixture | | |
| Clarithromycin | 0.500 | |
| Metronidazole | 0.500 | |
| Total antibiotics | | 1.000 |
| Citric acid | 0.035 | |
| Bibasic sodium phosphate bihydrate | 0.200 | |
| Mint essence | 0.010 | |
| Total | 1.245 | |
| Surfactant mixture | | |
| Maltodextrin | 1.000 | |
| Xylitol | 1.065 | |
| Mannitol | 0.490 | |
| Polysorbate 80 | 0.200 | 0.200 |
| Total | 2.55 | |
| Total of formulation | 4.000 | |

Preparation Method of Surfactant Mixture

Maltodextrin powders, mannitol and xylitol are granulated with a solution of polysorbate 80 in water in the proportions shown in the following table, and are then dried with fluidized bed to afford a surfactant mixture of the composition necessary for the formulation of the preparation.

| Surfactant mixture | g |
|---|---|
| Maltodextrin | 10.00 |
| Xylitol | 10.65 |
| Mannitol | 4.90 |
| Polysorbate 80 | 2.00 |
| Total | 27.55 |

Example 2—Preparation with Polysorbate/Antibiotics Ratio: 1:2.5

| Ingredients | Weight (g) | Active ingredients (g) |
|---|---|---|
| Antibiotic mixture | | |
| Clarithromycin | 0.500 | |
| Metronidazole | 0.500 | |
| Total antibiotics | | 1.000 |
| Citric acid | 0.035 | |
| Bibasic sodium phosphate bihydrate | 0.200 | |
| Mint essence | 0.010 | |
| Total | 1.245 | |
| Surfactant mixture | | |
| Maltodextrin | 1.000 | |
| Xylitol | 1.065 | |
| Mannitol | 0.290 | |
| Polysorbate 80 | 0.400 | 0.400 |
| Total | 2.755 | |
| Total formulation | 4.000 | |

Maltodextrin powders, mannitol and xylitol, dosed in proportions corresponding to the present composition, are granulated with a solution of polysorbate 80 in water and are then dried to afford the surfactant mixture, in the same way as in Example 1.

Example 3—Preparation with Polysorbate/Antibiotics Ratio: 1:1.25

| Ingredients | Weight (g) | Active ingredients (g) |
|---|---|---|
| Antibiotic mixture | | |
| Clarithromycin | 0.500 | |
| Metronidazole | 0.500 | |
| Total antibiotics | | 1.000 |
| Citric acid | 0.035 | |
| Bibasic sodium phosphate bihydrate | 0.200 | |
| Mint essence | 0.010 | |
| Total | 1.245 | |
| Surfactant mixture | | |
| Maltodextrin | 1.000 | |
| Xylitol | 0.665 | |
| Mannitol | 0.290 | |
| Polysorbate 80 | 0.800 | 0.800 |
| Total | 2.755 | |
| Total formulation | 4.000 | |

Maltodextrin powders, mannitol and xylitol, dosed in proportions corresponding to the present composition, are granulated with a solution of polysorbate 80 in water and are then dried to afford the surfactant mixture, in the same way as in Example 1.

Example 4—Preparation with Polysorbate/Antibiotics Ratio: 1:1

| Ingredients | Weight (g) | Active ingredients (g) |
|---|---|---|
| Antibiotic mixture | | |
| Clarithromycin | 0.500 | |
| Metronidazole | 0.500 | |
| Total antibiotics | | 1.000 |
| Citric acid | 0.035 | |
| Bibasic sodium phosphate bihydrate | 0.200 | |
| Mint essence | 0.010 | |
| Total | 1.245 | |
| Surfactant mixture | | |
| Maltodextrin | 1.000 | |
| Xylitol | 0.465 | |
| Mannitol | 0.290 | |
| Polysorbate 80 | 1.000 | 1.000 |
| Total | 2.755 | |
| Total formulation | 4.000 | |

Maltodextrin powders, mannitol and xylitol, dosed in proportions corresponding to the present composition, are granulated with a solution of polysorbate 80 in water and are then dried to afford the surfactant mixture, in the same way as in Example 1.

Example 5—Preparation with Polysorbate/Antibiotics Ratio: 1.25:1

| Ingredients | Weight (g) | Active ingredients (g) |
|---|---|---|
| Antibiotic mixture | | |
| Clarithromycin | 0.500 | |
| Metronidazole | 0.500 | |
| Total antibiotics | | 1.000 |
| Citric acid | 0.035 | |

| Ingredients | Weight (g) | Active ingredients (g) |
|---|---|---|
| Bibasic sodium phosphate bihydrate | 0.200 | |
| Mint essence | 0.010 | |
| Total Surfactant mixture | 1.245 | |
| Maltodextrin | 0.750 | |
| Xylitol | 0.465 | |
| Mannitol | 0.290 | |
| Polysorbate 80 | 1.250 | 1.250 |
| Total | 2.755 | |
| Total formulation | 4.000 | |

Maltodextrin powders, mannitol and xylitol, dosed in proportions corresponding to the present composition, are granulated with a solution of polysorbate 80 in water and are then dried to afford the surfactant mixture, in the same way as in Example 1.

Example 6—Preparation with Polysorbate/Antibiotics Ratio: 2:1

| Ingredients | Weight (g) | Active ingredients (g) |
|---|---|---|
| Antibiotic mixture | | |
| Clarithromycin | 0.300 | |
| Metronidazole | 0.300 | |
| Total antibiotics | | 0.600 |
| Citric acid | 0.035 | |
| Bibasic sodium phosphate bihydrate | 0.200 | |
| Mint essence | 0.010 | |
| Total Surfactant mixture | 0.845 | |
| Maltodextrin | 1.000 | |
| Xylitol | 0.655 | |
| Mannitol | 0.300 | |
| Polysorbate 80 | 1.200 | 1.200 |
| Total | 3.155 | |
| Total formulation | 4.000 | |

Maltodextrin powders, mannitol and xylitol, dosed in proportions corresponding to the present composition, are granulated with a solution of polysorbate 80 in water and are then dried to afford the surfactant mixture, in the same way as in Example 1.

Example 7—Preparation with Polysorbate/Antibiotics Ratio: 2.5:1

| Ingredients | Weight (g) | Active ingredients (g) |
|---|---|---|
| Antibiotic mixture | | |
| Clarithromycin | 0.250 | |
| Metronidazole | 0.250 | |
| Total antibiotics | | 0.500 |
| Citric acid | 0.035 | |
| Bibasic sodium phosphate bihydrate | 0.200 | |
| Mint essence | 0.010 | |
| Total Surfactant mixture | 0.745 | |
| Maltodextrin | 1.000 | |
| Xylitol | 0.705 | |
| Mannitol | 0.300 | |
| Polysorbate 80 | 1.250 | 1.250 |
| Total | 3.255 | |
| Total formulation | 4.000 | |

Maltodextrin powders, mannitol and xylitol, dosed in proportions corresponding to the present composition, are granulated with a solution of polysorbate 80 in water and are then dried to afford the surfactant mixture, in the same way as in Example 1.

B. Syrup: Bottle with Dosing Cap

For each one of the following examples a first mixture (Antibiotic mixture) is prepared, containing the antibiotics and part of the excipients, that is to be inserted in the dosing cap of a 20 ml bottle. The second mixture (Surfactant mixture), containing polysorbate 80 and another part of the excipients, is in the form of an aqueous solution, and is placed directly in the bottle. The two mixtures are prepared to be joined by the user just before the use, in order not to compromise the antibiotics stability in the solution.

Also in this case the division in two parts evidences that polysorbate 80 does not have a technological function, rather it is a true active ingredient which is prepared separately from the antibiotic mixture.

Example 8—Preparation with Polysorbate/Antibiotics Ratio: 1:5

| Ingredients | Weight (g) | Active ingredients (g) |
|---|---|---|
| Antibiotic mixture | | |
| Clarithromycin | 0.500 | |
| Metronidazole | 0.500 | |
| Total antibiotics | | 1.000 |
| Citric acid | 0.035 | |
| Bibasic sodium phosphate bihydrate | 0.200 | |
| Mint essence | 0.010 | |
| Total Surfactant mixture | 1.245 | |
| Xylitol | 2.000 | |
| Mannitol | 1.000 | |
| Polysorbate 80 | 0.200 | 0.200 |
| Water | q.s. to 20 ml | |

Example 9—Preparation with Polysorbate/Antibiotics Ratio: 1:2.5

| Ingredients | Weight (g) | Active ingredients (g) |
|---|---|---|
| Antibiotic mixture: same as in Example 8 | | 1.000 |
| Surfactant mixture | | |
| Xylitol | 2.000 | |
| Mannitol | 1.000 | |
| Polysorbate 80 | 0.400 | 0.400 |
| Water | q.s. to 20 ml | |

Example 10—Preparation with Polysorbate/Antibiotics Ratio: 1:1.25

| Ingredients | Weight (g) | Active ingredients (g) |
|---|---|---|
| Antibiotic mixture: as in Example 8 | | 1.000 |
| Surfactant mixture | | |
| Xylitol | 2.000 | |
| Mannitol | 1.000 | |
| Polysorbate 80 | 0.800 | 0.800 |
| Water | q.s. to 20 ml | |

Example 11—Preparation with Polysorbate/Antibiotics Ratio: 1:1

| Ingredients | Weight (g) | Active ingredients (g) |
|---|---|---|
| Antibiotic mixture: as in Example 8 | | 1.000 |
| Surfactant mixture | | |
| Xylitol | 2.000 | |
| Mannitol | 1.000 | |
| Polysorbate 80 | 1.000 | 1,000 |
| Water | q.s. to 20 ml | |

Example 12—Preparation with Polysorbate/Antibiotics: 2:1

| Ingredients | Weight (g) | Active ingredients (g) |
|---|---|---|
| Antibiotic mixture: as in Example 8 | | 1.000 |
| Surfactant mixture | | |
| Xylitol | 2.000 | |
| Mannitol | 1.000 | |
| Polysorbate 80 | 2.000 | 2.000 |
| Water | q.s. to 20 ml | |

Example 13—Preparation with Polysorbate/Antibiotics: 3:1

| Ingredients | Weight (g) | Active ingredients (g) |
|---|---|---|
| Antibiotic mixture: as in Example 8 | | 1.000 |
| Surfactant mixture | | |
| Xylitol | 2.000 | |
| Mannitol | 1.000 | |
| Polysorbate 80 | 3.000 | 3.000 |
| Water | q.s. to 20 ml | |

Formulations Containing Metronidazole and Polysorbate 80

A. 4 Grams Sachets of Powder Product

The preparation method is the same as for the formulations in sachets containing clarithromycin, metronidazole and polysorbate.

Example 14—Preparation with Polysorbate/Metronidazolo Ratio: 1:2.5

| Ingredients | Weight (g) | Active ingredients (g) |
|---|---|---|
| Antibiotic mixture | | |
| Metronidazole | 0.500 | 0.500 |
| Maltodextrin | 0.500 | |
| Citric acid | 0.035 | |
| Bibasic sodium phosphate bihydrate | 0.200 | |
| Mint essence | 0.010 | |
| Total | 1.245 | |
| Surfactant mixture | | |
| Maltodextrin | 1.000 | |
| Xylitol | 1.065 | |
| Mannitol | 0.490 | |
| Polysorbate 80 | 0.200 | 0.200 |
| Total | 2.755 | |
| Total formulation | 4.000 | |

Example 15—Preparation with Polysorbate/Metronidazole: 2.5:1

| Ingredients | Weight (g) | Active ingredients (g) |
|---|---|---|
| Antibiotic mixture | | |
| Metronidazole | 0.500 | 0.500 |
| Citric acid | 0.035 | |
| Bibasic sodium phosphate bihydrate | 0.200 | |
| Mint essence | 0.010 | |
| Total | 0.745 | |
| Surfactant mixture | | |
| Maltodextrin | 1.150 | |
| Xylitol | 0.565 | |

| Ingredients | Weight (g) | Active ingredients (g) |
|---|---|---|
| Mannitol | 0.290 | |
| Polysorbate 80 | 1.250 | 1.250 |
| Total | 3.255 | |
| Total formulation | 4.000 | |

B. Syrup: Bottle with Dosing Cap

The preparation method is the same as for the formulations in syrup containing clarithromycin, metronidazole and polysorbate.

Example 16—Preparation with Polysorbate/Metronidazole Ratio: 1:1

| Ingredients | Weight (g) | Active ingredients (g) |
|---|---|---|
| Antibiotic mixture | | |
| Metronidazole | 0.500 | 0.500 |
| Citric acid | 0.035 | |
| Bibasic sodium phosphate bihydrate | 0.200 | |
| Mint essence | 0.010 | |
| Total | 0.745 | |
| Surfactant mixture | | |
| Xylitol | 2.000 | |
| Mannitol | 1.000 | |
| Polysorbate 80 | 0.500 | 0.500 |
| Water | q.s. to 20 ml | |

Example 17—Preparation with Polysorbate/Metronidazole: 4:1

| Ingredients | Weight (g) | Active ingredients (g) |
|---|---|---|
| Antibiotic mixture: as in Example 16 | | 0.500 |
| Surfactant mixture | | |
| Xylitol | 2.000 | |
| Mannitol | 1.000 | |
| Polysorbate 80 | 2.000 | 2,000 |
| Water | q.s. to 20 ml | |

Formulations Containing Clarithromycin and Polysorbate 80

A. 4 Grams Sachets of Powder Product

The preparation method is the same as for the formulations in sachets containing clarithromycin, metronidazole and polysorbate.

Example 18—Preparation with Polysorbate/Clarithromycin Ratio: 1:2.5

| Ingredients | Weight (g) | Active ingredients (g) |
|---|---|---|
| Antibiotic mixture | | |
| Clarithromycin | 0.500 | 0.500 |
| Maltodextrin | 0.500 | |
| Citric acid | 0.035 | |
| Bibasic sodium phosphate bihydrate | 0.200 | |
| Mint essence | 0.010 | |
| Total | 1.245 | |
| Surfactant mixture: as in Example 14 | | 0.200 |
| Total formulation | 4.000 | |

Example 19—Preparation with Polysorbate/Clarithromycin: 2:1

| Ingredients | Weight (g) | Active ingredients (g) |
|---|---|---|
| Antibiotic mixture | | |
| Clarithromycin | 0.500 | 0.500 |
| Citric acid | 0.035 | |
| Bibasic sodium phosphate bi-hydrate | 0.200 | |
| Mint essence | 0.010 | |
| Total | 0.745 | |
| Surfactant mixture | | |
| Maltodestrine | 1.400 | |
| Xylitol | 0.565 | |
| Mannitol | 0.290 | |
| Polysorbate 80 | 1.000 | 1.000 |
| Total | 3.255 | |
| Total formulation | 4.000 | |

B. Syrup: Bottle with Dosing Cap

The preparation method is the same as for the formulations in syrup containing clarithromycin, metronidazole and polysorbate.

Example 20—Preparation with Polysorbate/Clarithromycin Ratio: 1:1.25

| Ingredients | Weight (g) | Active ingredients (g) |
|---|---|---|
| Antibiotic mixture | | |
| Clarithromycin | 0.500 | 0.500 |
| Citric acid | 0.035 | |
| Bibasic sodium phosphate bihydrate | 0.200 | |
| Mint essence | 0.010 | |
| Total | 0.745 | |
| Surfactant mixture | | |
| Xylitol | 2.000 | |
| Mannitol | 1.000 | |
| Polysorbate 80 | 0.400 | 0.400 |
| Water | q.s. to 20 ml | |

Example 21—Preparation with Polysorbate/Clarithromycin: 3:1

| Ingredients | Weight (g) | Active ingredients (g) |
|---|---|---|
| Antibiotic mixture: as in Example 20 | | 0.500 |
| Surfactant mixture | | |
| Xylitol | 2.000 | |
| Mannitol | 1.000 | |
| Polysorbate 80 | 1.500 | 2.000 |
| Water | q.s. to 20 ml | |

The specific features of the invention, as well as the advantages of the same in comparison with the solutions of the known techniques, will result more clearly with reference to the experimentation reported for merely exemplificative purposes below.

Evaluation of the Antibacterial Activity of the Proposed Combinations Against H. pylori In order to ascertain the performance of the proposed combinations of active ingredients according to the invention in the pharmacologic treatment of eradication of Helicobacter pylori, it has been hypothesized to start from the standard pharmacological treatments as previously described for the triple therapy, detecting the in vitro effectiveness of the antibiotic agents used in such therapy, alone or in combination with the anti-microbial additional agent proposed.

For the sensitivity tests 10 strains of H. pylori were used, the features of which are reported in the following Table 1.

As previously noted, the bacterial strains containing the cag pathogenicity island are much more virulent than those that do not contain it. The cag-positive strains and the cag-negative strains are so different from each other that for this species the concept of "quasi-species" has been created".

This is mainly the reason why when carrying our studies on the effectiveness of antibacterial agents on Helicobacter pylori it is necessary to test some representatives of both groups of bacterial clones (i.e., strains with the cag pathogenicity island and strains without the said island).

(table follows)

For the execution of the antibacterial activity tests against the various H. pylori strains, the test materials have been prepared as follows.

Polysorbate 80 has been solubilised in water at 5% concentration. Ferulic acid has been solubilised in TRIS buffer at 0.4% (weight/volume) concentration.

After further dilution in Brucella broth containing 10% bovine fetal serum, the samples were sterilized by filtration through membranes with 0.22 μm pores.

The various antibiotics, amoxicillin, metronidazole, clarithromycin and levofloxacin were used already dissolved, in their formulation for intravenous infusion. As the moment of the test the samples were diluted in double Brucella broth, in a volume of 100 μL, in "Microtiter" plates.

The various strains were cultured in Brucella agar with 10% fetal bovine serum in jars were a reduced oxygen tension atmosphere had been established, obtained with "Campypack" bags, at 37° C. for 48 hours At the time of the test, each strain was suspended in Brucella broth at the optical density corresponding to the McFarland opacity standard #4 (about $10^8$ CFU/ml) and further diluted 1:20 in the same broth ($5 \times 10^5$ CFU/ml approx.); 4 μL of each bacterial suspension were then added to the various dilutions of the samples; each well contained, thus, about $2 \times 10^5$ CFU/ml.

After incubation for one night in the same microaerophilic atmosphere at 37° C., 3 μL of each dilution were placed on agar plates of Brucella-bovine fetal serum, which were immediately incubated at 37° C. in the same atmosphere for 3-5 days.

The lowest concentration in broth of the test sampled whose subculture on agar showed the full absence of bacterial growth was considered to be the minimal bactericidal concentration. (MBC).

The results of several tests are gathered in the following Table 2.

| CagA status and resistances of the H. pylori strains examined and pathology of the corresponding patients | | | | | | | | | | |
|---|---|---|---|---|---|---|---|---|---|---|
| | H. pylori strains | | | | | | | | | |
| | CCUG 17874 (CagA+) | G50 (CagA−) | G21 (CagA−) | 4 Kb (CagA+) | Di Simpli (CagA+) | 10K (CagA+) | 328 (CagA+) | 328 Km (isogenic mutant CagA−) | M/C-R1 (CagA+) | M/C-R2 (CagA+) |
| Status CagA | + | − | − | + | + | + | + | − | + | + |
| Pathology | type strain | GCnA | GCnA | CG | GCE | CG | GC | | GCnA | GCnA |
| Resistance to antibiotic | met | − | − | − | − | − | − | − | met and clar | met and clar |

Legenda: GCnA, non-atrophic chronic gastritis; CG, gastric carcinoma; GCE, active chronic gastritis; met, metronidazole; clar, clarithromycin.

TABLE 2

Minimal bactericidal concentrations (MBC) of polysorbate 80, ferulic acid and some antibiotics against different strains of *H. pylori*

| Substance | H. pylori strains | | | | | | | | | |
|---|---|---|---|---|---|---|---|---|---|---|
| | CCUG 17874 | G50 | G21 | 4 Kb | Di Simpli MBC (µg/ml) | 10K | 328 | 328 Km | M/C-R1 | M/C-R2 |
| polysorbate 80 | 5.0 | 4.0 | 1.6 | 31 | 25 | 6.2 | 31-62 | 62 | 160 | 62 |
| clarithromycin | 0.25 | 0.2 | 0.2 | 0.1 | 0.4 | | 0.2 | | 320 | 2500 |
| metronidazole | 3.1 | | | | 10 | | 16 | | 40 | 320 |
| amoxicillin | | 0.04 | | | | 0.08 | | | | |
| levofloxacin | | 0.16 | | | | 0.31 | | | | |
| polysorbate/clarithromycin | 1.25/0.016 | | | | | | 31/0.025 | | 80/20 | 31/2.5 |
| polysorbate/metronidazole | | | | | | | 16/0.25 | | 80/4.0 | |
| polysorbate/amoxicillin | | 4/0.02 | | | | 6.2/0.08 | | | | |
| polysorbate/levofloxacin | | 4/0.08 | | | | 6.2/0.31 | | | | |
| ferulic acid in TRIS | 1250 | 1100 | 1100 | 1100 | 1100 | 1100 | 1250 | 1250 | 900-1100 | 800-900 |
| ferulic acid/clarithromycin | 625/0.125 | | | | | | | | | |
| ferulic acid/metronidazole | 625/1.6 | | | | 250/5 | | | | | |

From the data reported in the preceding table the following observations can be drawn.

- the MBC of clarithromycin vs. the multiresistant strain M/C-R2 drops from 2500 µg/ml to 2.5 µg/ml when the antibiotic is used in combination with polysorbate.
- the synergistic activity of polysorbate is shown with the sensitive strains as well; the MBCs of the antibiotics drop by 8-10 times when polysorbate and clarithromycin are used in combination (strains CCUG 17874 and 328).
- the MBCs of polysorbate, metronidazole and clarithromycin against the strain 328 are, respectively, 62 µg/ml, 16 µg/ml and 0.2 µg/ml; the MBCs of the polysorbate-metronidazole combination are 16 µg/ml and 0.25 µg/ml; those of the polysorbate-clarithromycin combination are 32 µg/ml and 0.025 µg/ml. This strain is resistant to metronidazole only. It may be seen that the activity of metronidazole combined with polysorbate increases 64 times and the activity of clarithromycin in combination with polysorbate increases 8 times.
- the MBCs of polysorbate, metronidazole and clarithromycin against the resistant strain M/C-R1 are respectively 160 µg/ml, 40 µg/ml, and 320 µg/ml. the MBCs of the combination polysorbate-metronidazole are 80 µg/ml and 4 µg/ml; those of the polysorbate-clarithromycin combination are 80 µg/ml and 20 µg/ml. The resistance levels to metronidazole and to clarithromycin were reduced, respectively, by 10 and 16 times.
- the MBCs of polysorbate and clarithromycin vs. the resistant strain M/C-R2 are, respectively, 62 µg/ml e 2500 µg/ml; those of the polysorbate-clarithromycin combination are 32 µg/ml and 2.5 µg/ml. In this case the MBC was reduced down to clarithromycin levels considered almost inactive (1 µg/ml, according to someone, 2 µg/ml, according to others).
- the fact that the combination with polysorbate greatly enhances the bactericidal activity of the two antibiotics metronidazole and clarithromycin has an immediate relevance as concerns metronidazole, since it has already been observed that low resistance levels to metronidazole can be overcome by increasing the dosage of the medicament. It may be hypothesized that also in the case of clarithromycin the reduction of resistance due to the combination with polysorbate is translated into a higher efficacy of the treatment.
- the amoxicillin/polysorbate 80 combination and the levofloxacin/polysorbate 80 combination, on the contrary, have shown an activity of a merely additive type. Considering the example of the strains G50 and 10K, the MBCs of polysorbate are respectively 4 µg/ml and 6.2 µg/ml. The MBCs of amoxicillin are 0.04 µg/ml and 0.08 µg/ml; those of the polysorbate/amoxicillin combination are 0.02 µg/ml (in another test, 2/0.04 µg/ml has been obtained) and 6.2/0.08 µg/ml. The MBCs of levofloxacin for the two strains are respectively 0.16 µg/ml and 0.31 µg/ml; those of the polysorbate/levofloxacin combination are 4/0.08 µg/ml and 6.2/0.31 µg/ml.

With reference to the same table, in connection with the experimentation with ferulic acid the following results were obtained.

Ferulic acid showed a bactericidal activity against all of the *H. pylori* strains, including the two metronidazole/clarithromycin-resistant strains. The MBCs range from 0.8 to 1.2 mg/ml.

The ferulic acid/polysorbate combination showed an activity of the additive type.

From the experimental study synthesized above it is possible to draw the following conclusions:

The polysorbate/metronidazole combination and the polysorbate/clarithromycin combination, differently from the combinations of polysorbate with other antibiotics, show a synergistic bactericidal activity, which is kept also against the strains resistant to the two antibiotics.

The antioxidant product of a natural origin ferulic acid is active as antibacterial against *H. pylori*, even if the combination ferulic acid/polysorbate shows a merely additive activity.

The present invention has been disclosed with particular reference to some specific embodiments thereof, but it should be understood that modifications and changes may be made by the persons skilled in the art without departing from the scope of the invention as defined in the appended claims.

The invention claimed is:

1. A method of treating an infection from *Helicobacter pylori*, comprising orally administering to a subject in need thereof a pharmaceutical composition containing, as active ingredients, polysorbate and an antibiotic selected from clarithromycin, metronidazole and a mixture of the same, characterized in that the weight ratio of polysorbate to antibiotic or mixture of antibiotics is from 2:5 to 4:1.

2. The method according to claim 1, wherein the said antibiotic is clarithromycin.

3. The method according to claim 1, wherein the said antibiotic is metronidazole.

4. The method according to claim 1, wherein the said polysorbate is polysorbate 80.

5. The method according to claim 4, wherein the pharmaceutical composition is formulated in a pharmaceutical preparation in the form of a solution, a colloidal suspension, an emulsion, a syrup or a granulate.

6. The method according to claim 5, wherein each liquid, semisolid or solid dosage unit in the said pharmaceutical composition contains from 500 to 750 mg of polysorbate and 500 mg of clarithromycin and/or 500 mg of metronidazole.

7. The method according to claim 4, wherein the pharmaceutical composition comprises, as a further active ingredient, ferulic acid.

8. A method of treating an infection of *Helicobacter pylori*, comprising orally administering to a subject in need thereof polysorbate and an antibiotic selected from clarithromycin, metronidazole and a mixture of the same, wherein the weight ratio of polysorbate to antibiotic or mixture of antibiotics is from 2:5 to 4:1.

9. The method according to claim 8, wherein the said antibiotic is a combination of clarithromycin and metronidazole.

10. The method according to claim 8, wherein the said antibiotic is clarithromycin.

11. The method according to claim 8, wherein the said antibiotic is metronidazole.

12. The method according to claim 8, wherein the said polysorbate is polysorbate 80.

13. The method according to claim 8, wherein the method comprises the eradication of *Helicobacter pylori*.

14. The method according to claim 13, wherein the said *Helicobacter pylori* belongs to a strain resistant to clarithromycin and/or to metronidazole.

* * * * *